United States Patent [19]

Scarborough

[11] Patent Number: 5,676,146
[45] Date of Patent: Oct. 14, 1997

[54] SURGICAL IMPLANT CONTAINING A RESORBABLE RADIOPAQUE MARKER AND METHOD OF LOCATING SUCH WITHIN A BODY

[75] Inventor: Nelson L. Scarborough, Ocean, N.J.

[73] Assignee: Osteotech, Inc., Eatontown, N.J.

[21] Appl. No.: 713,694

[22] Filed: Sep. 13, 1996

[51] Int. Cl.⁶ .................................................... A61B 6/00
[52] U.S. Cl. ............................ 128/654; 623/11; 623/16; 623/66
[58] Field of Search ...................... 623/11, 16, 18, 623/66; 606/77; 128/653.1, 654

[56] References Cited

U.S. PATENT DOCUMENTS

| | | |
|---|---|---|
| 3,829,904 | 8/1974 | Ling et al. . |
| 3,891,997 | 7/1975 | Herbert . |
| 3,922,726 | 12/1975 | Trentani et al. . |
| 4,123,806 | 11/1978 | Amstutz et al. . |
| 4,224,698 | 9/1980 | Hopson . |
| 4,450,592 | 5/1984 | Niederer et al. . |
| 5,306,304 | 4/1994 | Gendler .................................. 623/11 |
| 5,343,877 | 9/1994 | Park ........................................ 623/16 |
| 5,405,402 | 4/1995 | Dye et al. . |
| 5,425,762 | 6/1995 | Muller . |
| 5,476,880 | 12/1995 | Cooke et al. . |
| 5,507,813 | 4/1996 | Dowd et al. . |

*Primary Examiner*—Ruth S. Smith
*Attorney, Agent, or Firm*—Dilworth & Barrese

[57] ABSTRACT

A surgical implant containing a resorbable radiopaque marker enables the position and/or orientation of the implant to be readily determined by x-ray or other radiographic technique following its surgical implantation in the body.

17 Claims, No Drawings

SURGICAL IMPLANT CONTAINING A RESORBABLE RADIOPAQUE MARKER AND METHOD OF LOCATING SUCH WITHIN A BODY

BACKGROUND OF THE INVENTION

This invention is directed to a surgical implant, more particularly one containing a radiopaque marker which enables the position and/or orientation of the implant to be readily determined by x-ray or other radiographic technique following its surgical implantation in the body.

Osteoprosthetic implants are useful for repairing a variety of skeletal defects and irregularities. It may be necessary to confirm the location of an implant following its placement in the body. However, many osteoprosthetic implants are fabricated from materials, e.g., synthetic resins, that are transparent to radiographic imaging such as x-ray. Osteoprosthetic implants of this type have been provided with a radiopaque marker facilitating the determination of the position of the installed implant employing x-ray or other radiographic technique. See, e.g., U.S. Pat. Nos. 3,829,904, 3,891,997, 3,922,726, 4,123,806, 4,224,698, 4,450,592, 5,405,402, 5,425,762, and 5,476,880. The radiopaque markers in the implants described in these patents takes the form of a metal wire formed from a biologically compatible metal such as stainless steel.

SUMMARY OF THE INVENTION

In accordance with the present invention, an implant for repairing skeletal defects and irregularities is provided which comprises an implant fabricated from a radiolucent material and possessing a resorbable radiopaque marker, e.g., nondemineralized or partially demineralized bone particles. Unlike the metal wire radiopaque marker in the synthetic prostheses of the patents identified above, the implant of this invention has a radiopaque marker component which is resorbable in its entirety and may contribute to the healing of bone through natural processes.

DESCRIPTION OF THE PREFERRED EMBODIMENTS

The implant can be manufactured from any of several radiolucent resorbable or non-resorbable materials including demineralized bone sheet, particles, etc., collagen and collagen derivatives, plastic such as polyethylene cetabular cups.

In one embodiment of the present invention, the resorbable implant is manufactured from elongate demineralized bone particles as disclosed in U.S. Pat. No. 5,507,813, the contents of which are incorporated herein by reference. According to the method described in U.S. Pat. No. 5,507,813, elongate bone particles are obtained by milling from a section of whole bone, the particles are demineralized with acid in accordance with known and conventional procedures to provide substantially completely demineralized bone particles which are characteristically radiolucent and the bone particles are then formed into a shaped material possessing a definite geometrical configuration, e.g., a sheet possessing a square or rectangular shape. The sheet is formed by a wet-laying process the steps of which are as follows: slurrying a quantity of the demineralized elongate bone particles in a suitable liquid, e.g., water, organic protic solvent, aqueous solution such as physiological saline, etc., and optionally containing one or more biocompatible ingredients such as adhesives, fillers, plasticizers, flexibilizing agents, biostatic/biocidal agents, surface active agents, medically/surgically useful substances, etc., applying the slurry to a porous support, e.g., a flat perforate sheet, mesh screen or three-dimensional mold, through which excess slurry liquid drains thereby providing a coherent, shaped wetted mass of demineralized bone particles and, optionally, drying the wetted mass. The sheet material thus formed is relatively rigid when dry and, upon contact with a biocompatible liquid, e.g., water, saline solution, etc., becomes pliable and flexible thus making it readily conformable to a desired bone repair site.

The radiopaque marker which is to be incorporated into the resorbable implant of this invention is advantageously provided as native bone obtained from either human or animal bone, e.g., by cutting, milling, grinding or other suitable technique. The radiopaque marker can also be partially demineralized bone, the extent of demineralization being not so great as to substantially impair its radiopaque character. For example, partially demineralized bone containing not less than about 50 weight percent of its original mineral content can be utilized as the radiopaque component of the implant of this invention. The radiopaque marker can also be a resorbable calcium-based mineral, e.g., hydroxyapatite, tricalcium phosphate, etc., or other resorbable inorganic material. The radiopaque marker is preferably provided in particulate form with an average particle size of from about 0.1 mm to about 10 mm and preferably from about 1 mm to about 5 mm. The radiopaque marker can be shaped in the form of spherical, quasi-spherical, cuboid, rectangular or any other shape which may be useful.

The radiopaque marker can be incorporated into the resorbable implant at any stage in the manufacture of the latter, e.g., in the case of a bone sheet manufactured in accordance with aforementioned U.S. Pat. No. 5,507,813, by introduction into the slurry from which the bone sheet is made. The radiopaque marker can also be incorporated into the milled bone particles prior to their demineralization and formation into the bone sheet. However, as will be recognized, the radiopaque marker in this embodiment must be able to survive or be resistant to the demineralization process. In the case of a radiopaque marker made up of bone particles, by making such particles larger and/or thicker than the elongate bone particles intended for demineralization, it is possible to limit the extent of their demineralization so that they still contain sufficient inorganic matter to render them radiopaque while the elongate bone particles undergo complete, or nearly complete, demineralization. Another method of imparting resistance to demineralization to bone particles intended to function as the radiopaque marker is to coat the particles with a substance that is less susceptible to acid attack.

When incorporating the radiopaque marker into the resorbable implant, the marker can be arranged within the implant in a predetermined pattern, e.g., a geometric pattern such as a grid. This can be readily accomplished by use of a template placed over the implant during a processing step so that marker material that is poured or cast over the implant is only imbedded in desired areas. The usefulness of a predetermined pattern for the markers is to render the implant easily distinguishable from other surrounding structures in situ.

In the case of a resorbable implant which is fabricated from demineralized bone, application of the implant to the site of a bone defect, e.g., one resulting from injury, infection, malignancy or developmental malformation, leads to new bone ingrowth by one or more biological mechanisms such as osteogenesis, osteoconduction and/or osteoinduction or by one or more physical mechanisms such as providing a physical barrier to soft tissue ingrowth, presenting a support or scaffolding for new bone growth, etc.

Upon implantation of the implant into the body at a defect site, the implant can be viewed by using any of several known and conventional radiographic techniques such as x-ray imaging. In the case of x-ray imaging, the radiopaque marker is displayed on the exposed and developed x-ray film as white spots allowing the location and/or the orientation of the implant to be accurately determined.

The implant of this invention can be utilized in a wide variety of orthopaedic, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. These materials can be sutured or stapled in place for anchoring purposes and serve in guided tissue regeneration or as barrier materials.

The following examples are illustrative of the resorbable implant of this invention.

EXAMPLE 1

A sheet fabricated from demineralized elongate bone particles is manufactured according to the method described in U.S. Pat. No. 5,507,813. While the sheet is being wet-laid nondemineralized bone particles that have been classified to a predetermined range are added thereto. The mineralized particles are uniformly distributed within the wet sheet which is then subjected to the remaining manufacturing operations described in the aforesaid patent. The resultant flexible sheets are then cut into implant-sized pieces.

EXAMPLE 2

A small sheet from Example 1 is rehydrated and implanted into an animal at a calvarial defect site. The site is then sutured closed and the skull is x-rayed. The mineralized particles are displayed on the resultant x-ray film as white spots allowing the location of the implant to be precisely determined.

EXAMPLE 3

The nondemineralized bone particles in Example 1 can be incorporated into the wet-laid sheet in a regular pattern such as a grid with 5 mm spaces between particles. When the sheet processing is completed and a small sheet segment is rehydrated and implanted as in Example 2, the position/ orientation of the sheet segment is more easily determined via x-ray imaging due to the regular pattern of the radiopaque nondemineralized particles.

EXAMPLE 4

The nondemineralized particles of Example 1 can be distributed in a flowable osteogenic composition which is comprised of demineralized bone particles and an inert carrier such as glycerol.

What is claimed is:

1. A surgical implant for surgical implantation in the body, the implant being fabricated from radiolucent material and possessing a resorbable radiopaque marker.

2. The implant of claim 1 wherein the radiolucent material is resorbable.

3. The implant of claim 2 wherein the resorbable material is demineralized bone or collagen.

4. The implant of claim 2 wherein the resorbable material is a flexible sheet of demineralized bone.

5. The implant of claim 1 which possesses a definite geometrical configuration.

6. The implant of claim 1 wherein the resorbable radiopaque marker comprises nondemineralized or partially demineralized bone particles.

7. The implant of claim 6 wherein the nondemineralized or partially demineralized bone particles are selected from the group consisting of human and animal bone.

8. The implant of claim 6 wherein the nondemineralized or partially demineralized bone particles are of a predetermined shape selected from the group consisting of spherical, quasi-spherical, cuboid, tube, fiber, spiral and rectangular.

9. The implant of claim 6 wherein the partially demineralized bone particles contain not less than about 20 weight percent residual inorganic matter.

10. The implant of claim 1 wherein the resorbable radiopaque marker is a calcium-based mineral selected from the group consisting of hydroxyapatite, tricalcium phosphate, fluorapatite and their mixtures.

11. The implant of claim 1 wherein the resorbable radiopaque marker is arranged within the implant in accordance with a predetermined pattern.

12. The implant of claim 11 wherein the predetermined pattern is a grid.

13. A method of determining the location and/or orientation of a surgical implant within a body which comprises:
    a) surgically implanting within a body an implant fabricated from radiolucent material containing a resorbable radiopaque marker; and,
    b) post-surgically determining the location and/or orientation of the implant by a radiographic technique.

14. The method of claim 13 wherein radiolucent material is resorbable.

15. The method of claim 13 wherein the radiographic technique is x-ray imaging.

16. The method of claim 13 wherein the radiopaque marker is arranged within the implant in accordance with a predetermined pattern.

17. The method of claim 16 wherein the predetermined pattern is a grid.

* * * * *

REEXAMINATION CERTIFICATE (4047th)

United States Patent [19]
Scarborough

[11] B1 5,676,146
[45] Certificate Issued Apr. 18, 2000

[54] SURGICAL IMPLANT CONTAINING A RESORBABLE RADIOPAQUE MARKER AND METHOD OF LOCATING SUCH WITHIN A BODY

[75] Inventor: Nelson L. Scarborough, Ocean, N.J.

[73] Assignee: Osteotech, Inc., Eatontown, N.J.

Reexamination Request:
No. 90/005,222, Jan. 15, 1999

Reexamination Certificate for:
Patent No.: 5,676,146
Issued: Oct. 14, 1997
Appl. No.: 08/713,694
Filed: Sep. 13, 1996

[51] Int. Cl.⁷ .................................................. A61B 6/00

[52] U.S. Cl. ..................... 600/431; 623/11.11; 623/16.11

[56] References Cited

U.S. PATENT DOCUMENTS

| | | | |
|---|---|---|---|
| 4,627,853 | 12/1986 | Campbell et al. | 623/16 |
| 4,709,703 | 12/1987 | Lazarow et al. . | |
| 4,795,463 | 1/1989 | Gerow . | |
| 5,108,399 | 4/1992 | Eitenmuller et al. . | |
| 5,366,507 | 11/1994 | Sottosanti | 623/16 |
| 5,441,517 | 8/1995 | Kensey et al. . | |

FOREIGN PATENT DOCUMENTS

| | | |
|---|---|---|
| 0405429 | 1/1991 | European Pat. Off. . |
| 296 08 321 U | 8/1996 | Germany . |
| WO94/21196 | 9/1994 | WIPO . |

*Primary Examiner*—Ruth S. Smith

[57] ABSTRACT

A surgical implant containing a resorbable radiopaque marker enables the position and/or orientation of the implant to be readily determined by x-ray or other radiographic technique following its surgical implantation in the body.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 10, 11, 14 are cancelled.

Claims 1, 8, 9, 12, 13 are determined to be patentable as amended.

Claims 2–7, 15–17, dependent on an amended claim, are determined to be patentable.

New claims 18–24 are added and determined to be patentable.

1. A surgical implant for surgical implantation in the body, the implant being fabricated from radiolucent material and possessing a resorbable *particulate* radiopaque marker *arranged within the radiolucent material in a predetermined geometric pattern.*

8. [The implant of claim 6] *A surgical implant for surgical implantation in the body, the implant being fabricated from radiolucent material and possessing a resorbable radiopaque marker, the radiopaque marker including nondemineralized or partially demineralized bone particles* wherein the nondemineralized or partially demineralized bone particles are of a predetermined shape selected from the group consisting of spherical, quasi-spherical, cuboid, tube, fiber, spiral and rectangular.

9. [The implant of claim 6] *A surgical implant for surgical implantation in the body, the implant being fabricated from radiolucent material and possessing a resorbable radiopaque marker, the radiopaque marker including partially demineralized bone particles* wherein the partially demineralized bone particles contain not less than about 20 weight percent residual inorganic matter.

12. The implant of claim [11] *1* wherein the predetermined pattern is a grid.

13. A method of determining the location and/or orientation of a surgical implant within a body which comprises:
   a) surgically implanting within a body an implant fabricated from *particles of a* radiolucent material [containing a resorbable radiopaque marker] *uniformly distributed with a radiopaque marker of particles of nondemineralized or partially nondemineralized bone*; and
   b) post-surgically determining the location and/or orientation of the implant by a radiographic technique.

*18. A surgical implant for surgical implantation in the body comprising nondemineralized or partially demineralized bone particles and demineralized bone particles uniformly distributed in an inert carrier.*

*19. A surgical implant for surgical implantation in the body according to claim 18 wherein the inert carrier is glycerol.*

*20. A surgical implant for implantation in the body according to claim 18 wherein the implant includes collagen.*

*21. A surgical implant for surgical implantation in the body, the implant comprising particles of a radiolucent material in substantially uniform admixture with particles of nondemineralized or partially demineralized bone.*

*22. A surgical implant for surgical implantation in the body according to claim 21 wherein the radiolucent material is demineralized bone.*

*23. A surgical implant for surgical implantation in the body according to claim 21 wherein the implant possesses a definite geometrical configuration.*

*24. A surgical implant comprising radiolucent material and a resorbable particulate radiopaque marker arranged within the radiolucent material, wherein the radiolucent material includes demineralized bone and the radiopaque marker includes non-demineralized or partially demineralized bone.*

* * * * *

(12) EX PARTE REEXAMINATION CERTIFICATE (6066th)
United States Patent
Scarborough

(10) Number: US 5,676,146 C2
(45) Certificate Issued: Dec. 25, 2007

(54) SURGICAL IMPLANT CONTAINING A RESORBABLE RADIOPAQUE MARKER AND METHOD OF LOCATING SUCH WITHIN A BODY

(75) Inventor: Nelson L. Scarborough, Ocean, NJ (US)

(73) Assignee: Osteotech, Inc., Eatontown, NJ (US)

Reexamination Request:
No. 90/006,806, Oct. 9, 2003

Reexamination Certificate for:
Patent No.: 5,676,146
Issued: Oct. 14, 1997
Appl. No.: 08/713,694
Filed: Sep. 13, 1996

Reexamination Certificate B1 5,676,146 issued Apr. 18, 2000

(51) Int. Cl.
*A61F 2/28* (2006.01)
*A61F 2/02* (2006.01)
*A61F 2/00* (2006.01)
*A61B 6/00* (2006.01)
*A61B 6/12* (2006.01)
*A61B 19/00* (2006.01)

(52) U.S. Cl. .................... 600/431; 623/1.34; 623/11.11; 623/16.11
(58) Field of Classification Search ................. 600/431; 623/1.34, 11.11, 16.11
See application file for complete search history.

(56) References Cited

U.S. PATENT DOCUMENTS

| 4,627,853 | A | * | 12/1986 | Campbell et al. | ............ 128/898 |
| 4,824,939 | A | * | 4/1989 | Simpson | ...................... 530/356 |
| 5,441,517 | A | * | 8/1995 | Kensey et al. | ............... 606/213 |
| 5,507,813 | A | * | 4/1996 | Dowd et al. | ............. 523/23.63 |
| 5,510,396 | A | * | 4/1996 | Prewett et al. | ............... 523/113 |

OTHER PUBLICATIONS

Urist et al., Bone Formation in Implants of partially and Wholly Demineralized Bone Matrix, Clinical Orthopaedics and Related Research, vol. 71, pp. 271–278 (1970).*

Grafton™ Allogenic Bone Matrix (ABM), Advertising Brochure, *Advanced Processing of Human Allograft Bone*, Osteotech, Inc., 1992.

Frenkel et al., *Use of Demineralized Bone Matrix Gel to Enhance Spine Fusion*, $19^{th}$ Annual Meeting of the Society for Biomaterials, Apr. 28–May 2, 1993, Birmingham, AL, p. 162.

Stevenson et al., *Long Bone Defect Healing Induced By a New Formulation of Rat Demineralized Bone Matrix Gel*, $40^{th}$ Annual Meeting, Orthopedic Research Society, Feb. 21–24, 1994, New Orleans, LA, p. 205–35.

* cited by examiner

*Primary Examiner*—David O. Reip

(57) ABSTRACT

A surgical implant containing a resorbable radiopaque marker enables the position and/or orientation of the implant to be readily determined by x-ray or other radiographic technique following its surgical implantation in the body.

US 5,676,146 C2

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–7, 9 and 12 is confirmed.

Claims 10, 11 and 14 were previously cancelled.

Claims 8, 13, 18, 21 and 24 are determined to be patentable as amended.

Claims 15–17, 19, 20, 22 and 23, dependent on an amended claim are determined to be patentable.

New claims 25–28 are added and determined to be patentable.

8. [A] *An osteogenic* surgical implant for surgical implantation in the body, the implant being fabricated from radiolucent material and possessing a resorbable radiopaque [marker] *material*, the radiopaque [marker] *material* including nondemineralized or partially demineralized *allograft* bone particles *with an average particle size from about 0.1 mm to about 10 mm and being provided in sufficient quantity for use as a marker*, wherein the nondemineralized or partially demineralized *allograft* bone particles are of a predetermined shape selected from the group consisting of spherical, quasi-spherical, cuboid, tube, fiber, spiral and rectangular.

13. A method of determining the location and/or orientation of [a] *an osteogenic* surgical implant within a body which comprises:
   a) surgically implanting within a body an *osteogenic* implant fabricated from [particles of] a radiolucent material [uniformly distributed with] *comprising allograft bone particles and* a radiopaque [marker of] *material comprising* particles of nondemineralized or partially nondemineralized allograft bone, *the radiopaque material being uniformly distributed within the radiolucent material, wherein the radiopaque material is provided in sufficient quantity for use as a marker*; and
   b) post-surgically determining the location and/or orientation of the implant by a radiographic technique.

18. [A] *An* osteogenic surgical implant for surgical implantation in the body comprising *a radiopaque material comprising* nondemineralized or partially demineralized *allograft* bone particles and *a radiolucent material including* demineralized *allograft* bone particles, *the radiopaque material and radiolucent material being* uniformly distributed in an inert carrier, *wherein the radiopaque material is provided in sufficient quantity for use as a marker*.

21. [A] *An* osteogenic surgical implant for surgical implantation in the body, the implant comprising particles of a radiolucent material *including demineralized allograft bone particles* in substantially uniform admixture with *a radiopaque material including* particles of nondemineralized or partially demineralized *allograft* bone, *wherein the radiopaque material is provided in sufficient quantity for use as a marker*.

24. [A] *An* osteogenic surgical implant comprising radiolucent material and a resorbable particulate radiopaque marker arranged within the radiolucent material, wherein the radiolucent material includes demineralized *allograft* bone and the a radiopaque marker includes *particles of* nondemineralized or partially demineralized *allograft* bone, *the particles of nondemineralized or partially demineralized allograft bone being provided in sufficient quantities for use as a marker*.

*25. An osteogenic surgical implant for surgical implantation in the body comprising nondemineralized or partially demineralized allograft bone particles and demineralized allograft bone particles uniformly distributed in an inert carrier, the nondemineralized or partially demineralized allograft bone particles being provided in sufficient quantities for use as a marker, the surgical implant being stored in a package for subsequent implantation.*

*26. An osteogenic surgical implant for surgical implantation in the body, the implant comprising particles of a radiolucent material in a substantially uniform admixture with particles of nondemineralized or partially demineralized bone, wherein the particles of nondemineralized or partially demineralized bone are provided in sufficient quantities for use as a radiopaque marker, the surgical implant being stored in a package for subsequent implantation.*

*27. An osteogenic surgical implant comprising radiolucent material and a resorbable particulate radiopaque material arranged within the radiolucent material, wherein the radiolucent material includes demineralized allograft bone and the radiopaque material includes nondemineralized or partially demineralized allograft bone particles, wherein the radiopaque material is provided in sufficient quantity for use as a marker, the surgical implant being stored in a package for subsequent implantation.*

*28. The surgical implant of claim 18 wherein the surgical implant is packaged in the wet state.*

\* \* \* \* \*

(12) EX PARTE REEXAMINATION CERTIFICATE (10457th)

United States Patent
Scarborough

(10) Number: US 5,676,146 C3
(45) Certificate Issued: Dec. 29, 2014

(54) SURGICAL IMPLANT CONTAINING A RESORBABLE RADIOPAQUE MARKER AND METHOD OF LOCKING SUCH WITHIN A BODY

(75) Inventor: Nelson L. Scarborough, Ocean, NJ (US)

(73) Assignee: Warsaw Orthopedic, Inc., Warsaw, IN (US)

Reexamination Request:
No. 90/013,135, Jan. 24, 2014

Reexamination Certificate for:
Patent No.: 5,676,146
Issued: Oct. 14, 1997
Appl. No.: 08/713,694
Filed: Sep. 13, 1996

Reexamination Certificate C1 5,676,146 issued Apr. 18, 2000

Reexamination Certificate C2 5,676,146 issued Dec. 25, 2007

(51) Int. Cl.
*A61F 2/28* (2006.01)
*A61F 2/02* (2006.01)
*A61F 2/00* (2006.01)
*A61B 6/00* (2006.01)
*A61B 6/12* (2006.01)
*A61B 19/00* (2006.01)

(52) U.S. Cl.
USPC ..... 600/431; 623/1.34; 623/11.11; 623/16.11

(58) Field of Classification Search
None
See application file for complete search history.

(56) References Cited

To view the complete listing of prior art documents cited during the proceeding for Reexamination Control Number 90/013,135, please refer to the USPTO's public Patent Application Information Retrieval (PAIR) system under the Display References tab.

*Primary Examiner* — Catherine S. Williams

(57) ABSTRACT

A surgical implant containing a resorbable radiopaque marker enables the position and/or orientation of the implant to be readily determined by x-ray or other radiographic technique following its surgical implantation in the body.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 13, 15, 18, 21, 22, 25, 26 and 28 is confirmed.

Claims 10, 11 and 14 were previously cancelled.

Claims 1-9, 12, 16-17, 19-20, 23-24 and 27 were not reexamined.

\* \* \* \* \*